US006239287B1

(12) United States Patent
Dolan et al.

(10) Patent No.: US 6,239,287 B1
(45) Date of Patent: May 29, 2001

(54) PREPARATION OF PHOSPHONIUM COMPOUNDS AS INTERMEDIATES FOR GLYCINE ANTAGONISTS

(75) Inventors: Simon Charles Dolan, Rickmansworth (GB); Paolo Maragni, Virgilio; Alcide Perboni, S. Giorgio di Mautove, both of (IT)

(73) Assignee: Glaxo Wellcome SpA, Verona (IT)

( * ) Notice: Subject to any disclaimer, the term of this patent is extended or adjusted under 35 U.S.C. 154(b) by 0 days.

(21) Appl. No.: 09/367,874

(22) PCT Filed: Mar. 3, 1998

(86) PCT No.: PCT/EP98/01147

§ 371 Date: Sep. 7, 1999

§ 102(e) Date: Sep. 7, 1999

(87) PCT Pub. No.: WO98/39341

PCT Pub. Date: Sep. 11, 1998

(30) Foreign Application Priority Data

Mar. 5, 1997 (GB) .................................................. 9704499

(51) Int. Cl.$^7$ ...................................................... C07F 9/50
(52) U.S. Cl. .............................................................. 548/412
(58) Field of Search ............................................. 548/412

(56) References Cited

U.S. PATENT DOCUMENTS 5,359,089    10/1994   Kamhi .

FOREIGN PATENT DOCUMENTS

| 0 204 964 | 12/1986 | (EP) . |
| 0 532 767 | 3/1993 | (EP) . |
| 761673 * | 12/1997 | (EP) . |
| WO 95 10517 | 4/1995 | (WO) . |
| 9839327 * | 9/1998 | (WO) . |
| 9839341 * | 9/1998 | (WO) . |

OTHER PUBLICATIONS

H. Wamhoff et al., "3–Alkyliden–2–pyrrolidone durch Wittig–Reaktion" Synthesis., No. 5, May 1976 Stuttgart DE, XP002067178.

* cited by examiner

*Primary Examiner*—Deborah C. Lambkin
*Assistant Examiner*—Donya N. Wright
(74) *Attorney, Agent, or Firm*—Bacon & Thomas

(57) ABSTRACT

A process for the preparation of the phosphonium compound of formula (1), which comprises reacting N-phenylpyrrolidinone (II), with pyridinium bromide perbromide, in the presence of a tertiary organic base and a suitable lewis acid and then treating the resultant bromo derivative (III) with the phosphine (IV, $R_1R_2R_1P$) and the use of compound (I) when so prepared for the preparation of the glycine antagonist.

14 Claims, No Drawings

PREPARATION OF PHOSPHONIUM COMPOUNDS AS INTERMEDIATES FOR GLYCINE ANTAGONISTS

This application is a 371 of PCT/EP98/01147 filled Mar. 3, 1998.

This invention relates to improvements in the process for the preparation of a glycine antagonist.

WO 95/10517 describes inter alia the compound (E) 4,6-dichloro-3-(2-oxo-1-phenylpyrrolidine-3-ylidene methyl)-1H-indole-2-carboxylic acid (Compound A) and physiologically acceptable salts thereof, a potent antagonist at the strychrine insensitive glycine binding site associated with the NMDA receptor complex.

The present invention relates to a particularly convenient process for the preparation of an intermediate for use in the synthesis of Compound A and salts thereof.

Thus the present invention provides a process for the preparation of the phosphonium compound of formula (I) wherein each of $R_1$, $R_2$ and $R_3$ independently represent a $C_{1-12}$alkyl or phenyl group.

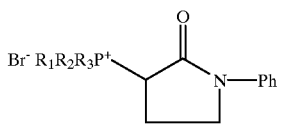

(I)

which comprises bromination of the N-phenylpyrrolidinone (II),

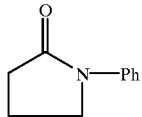

(II)

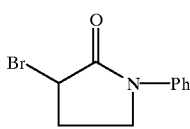

(III)

with pyridinium bromide perbromide, in the presence of a tertiary organic base and a suitable lewis acid and then treating the resultant bromo derivative (III) with the phosphine (IV, $R_1R_2R_3P$) wherein $R_1,R_2$ and $R_3$ have the meanings defined above.

The bromination step in the process is conveniently carried out in a solvent such as dichloromethane, acetonitrile, an ether e.g. tetrahydrofuran or t-butylmethyl ether, dimethoxyethane or a mixture of two or more solvents e.g. dichloromethane and acetonitrile and at a temperature within the range −10° to +20° e.g. 0–5°.

Examples of suitable tertiary organic bases for use in the reaction include the diamines $R_4R_5N(CH_2)_nNR_6R_7$(wherein $R_4$, $R_5$, $R_6$ and $R_7$ each independently represent a $C_{1-4}$ alkyl group e.g. methyl, ethyl, propyl or butyl group and n is an integer from 2 to 6), such as an $N,N,N^1N^1$-tetralkylethylenediamine e.g. $N,N,N^1N^1$tetramethylethylenediamine, tri $C_{1-4}$alkylamines such as triethylamine, diethylmethylamine or di-isopropylethylamine, or an optionally substituted pyridine such as pyridine or lutidine e.g. 2,6-lutidine. Conveniently the tertiary organic base is $N,N,N^1N^1$-tetramethylethylenediamine.

Examples of suitable Lewis acids for use in the reaction include a tri $C_{1-4}$alkylsilyl trifluoromethanesulphate (tri $C_{1-4}$ alkylsilyltriflate) e.g. trimethylsilyltriflate or tri $C_{1-4}$ alkylsilylbromide, e.g. trimethylsilylbromide. Conveniently the Lewis acid is a tri $C_{1-4}$ alkylsilyltriflate and more particularly trimethylsilyltriflate.

The reaction of the bromo derivate (III) with the phosphine (IV) is conveniently carried out in a solvent such as an ester e.g. ethyl acetate or an ether e.g. butyl methyl ether or tetrahydrofuran, or toluene or mixtures thereof and with heating e.g. 40° up to reflux.

Examples of suitable phosphines (IV) wherein $R_1$, $R_2$ and $R_3$ are $C_{1-12}$ alkyl includes those where $R_1$, $R_2$ and $R_3$ are the same, for example tri-methylphosphine, triethylphosphine, tri-n-propylphospine tri-tert-butylphosphine, tri-hexylphosphine, tri-n-octylphosphine, or tri-dodecylphosphine. Conveniently the phosphine (IV) is a tri-phenylphosphine or more particularly a tri $C_{1-6}$alkylphosphine and more especially tri-n-butylphosphine.

Conveniently in this process the bromination reaction mixture is treated with an aqueous solution of an inorganic base e.g. an alkali metal carbonate or bicarbonate e.g. sodium carbonate or sodium bicarbonate and the required bromo derivative (III) isolated in the organic phase before reaction with the phosphine (IV).

The process according to the invention provides a particularly convenient method for preparing compounds of formula (I) having the high degree of purity required for an intermediate for use in the manufacture of a pharmaceutical product.

In a preferred embodiment of the invention the bromination of N-phenyl pyrrolidinone is carried out with pyridinum bromide perbromide in dichloromethane in the presence of trimethylsilyltriflate and $N,N,N^1,N^1$-tetramethylethylenediamine at a temperature within the range 0 to 5° C. the subsequent reaction with the phosphine (IV) e.g. tributylphosphine is carried out in ethyl acetate with heating e.g. at reflux.

In this embodiment the bromination product is conveniently isolated by treating the reaction mixture with an aqueous solution of an inorganic base e.g. an alkali metal carbonate or bicarbonate e.g. sodium carbonate or sodium bicarbonate, the organic phase separated, dried and concentrated. The isolated product used without further purification, is then converted into the required phosphonium compound of formula (I) by reaction with phosphine (IV) in a suitable solvent e.g. ethyl acetate with heating e.g. at reflux.

The phosphonium compound (I) may be conveniently isolated from the cooled reaction mixture by filtration and used directly without further purification in the preparation of compound A. Thus in a further aspect the invention provides a process for the preparation of Compound A which comprises reacting a phosphonium compound of formula (I), when prepared from N-phenylpyrrolidinone (II) by the process described above, with the aldehyde (V) wherein $R_8$ is a carboxyl protecting group.

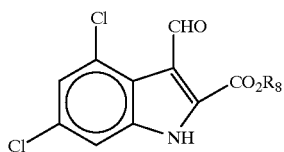

(V)

in the presence of a suitable base e.g. 1,8-diazobicylo[5.4.0] undec-7-ene and in a solvent e.g. THF or an alkanol e.g. ethanol (IMS) or isopropanol, followed by removal of the carboxyl protecting group and isolation of the compound either in the form of the free acid or a physiologically acceptable salt thereof e.g sodium salt.

A particularly convenient phosphonium compound (I) for use in the preparation of Compound A is that wherein $R_1$, $R_2$ and $R_3$ each represent an n-butyl group.

Suitable carboxyl protecting groups $R_8$ include allyl, alkyl, trialkysilylalkyl or arylmethyl groups such as benzyl, nitrobenzyl, benzhydryl or trityl.

These carboxyl protecting groups may be removed by conventional means. Thus, for example when $R_8$ is an alkyl group this may be removed by hydrolysis using an alkali metal hydroxide e.g. lithium hydroxide or sodium hydroxide in a solvent such as an alkanol e.g. an isopropanol.

A salt of compound A may be prepared from the corresponding free acid in a conventional manner. For example the sodium salt may be prepared by reaction of the free acid with sodium hydroxide in a suitable solvent e.g. isopropanol.

The phosphonium compounds of formula (I) wherein $R_1$, $R_2$ and $R_3$ each represent $C_{1-12}$alkyl wherein $R_1$, $R_2$ and $R_3$ each represent $C_{1-12}$alkyl, are novel and represent a further aspect of the invention. A preferred phosphonium compound of formula (I) is that where $R_1$, $R_2$ and $R_3$ each represent an n-butyl group.

In order that the invention may be more fully understood the following examples are given by way of illustration only.

INTERMEDIATE 1

Ethyl (E)4,6-dichloro-3-(2-oxo-1-phenylpyrrolidin-3-ylidenemethyl)-1H-indole 2-carboxylate 1,8-Diazabicyclo[5.4.0]undec-7-ene (1.24 ml) was added to a mixture of ethyl 3 formyl-4,6-dichloroindole-2-carboxylate (2 g) and tributyl(2-oxo-1-phenylpyrrolin-1-yl) phosphonium bromide to reflux and refluxed for 8 hr before cooling slowly to room temperature. The reaction mixture was cooled to approx. 5° C. using an ice/water bath and aged at 0–5° C. for 2 hr. The precipitate was filtered under vacuum and washed with isopropanol (7.5 ml). The product was dried in a vacuum oven at 40° C. to give the title compound as a white crystalline solid (1.95 g).

EXAMPLE 1

Tributyl (2-oxo-1-phenylpyrrolidin-1-yl) phosphonium bromide

N,N,N$^1$N$^1$-Tetramethylethylene diamine (23.3 ml) was added to a solution of N-phenylpyrrolidinone (5 g) in dichloromethane (50 ml the solution was cooled to 0–5° and trimethylsilyl triflate (8.4 ml) was added over ca 20 mins maintaining the temperature in the range 0–5°. The resultant solution was stirred for 10 mins and a solution of pyridinium bromide perbromide (13 g) in acetonitrile (20 ml) was added over ca 20 mins maintaining the temperature in the range 0–10°.The resultant suspension was stirred at 0–5° for ca 60 mins. Aqueous sodium bicarbonate solution (50 ml) was added, cautiously. The mixture was stirred for ca 5 mins and the layers are separated.The aqueous phase was diluted with water (20 ml) and back extracted with dichloromethane (20 ml). The combined organic phases were washed with further sodium bicarbonate solution (50 ml), 2M hydrochloric acid (2×50 ml) and water (50 ml), back extracting each wash with dichloromethane (10 ml). The organic solution was dried (MgSO$_4$) and concentrated on a rotavapor. The red/brown solid was stirred with ethyl acetate (50 ml) and warmed to give a solution which was then cooled and tributylphosphine (8.5 ml) was added.The solution was heated to reflux and maintained at reflux for 2.5 hours. The solution was allowed to cool to room temperature and was then cooled to 0–5°. The resulting suspension was aged at 0–5° for ca 60 min. The product was isolated by vacuum filtration and then washed with ethyl acetate:t-butylmethylether (1:1, 40 ml) and dried in a vacuum oven at 45° to give the title compound as a white crystalline solid (10.12 g), mp 127–128°.

EXAMPLE 2

Tributyl (2-oxo-1-phenylpyrrolidin-1-yl) phosphonium bromide

Tetramethylethylenediamine (34.5 ml) was added to a solution of N-phenylpyrrolidinone (10 g) in dichloromethane (100 ml). The solution was cooled to 0–5° and trimethylsilyl trifluoromethanesulphonate (12.3 ml) was added, maintaining the temperature in the range 0–5°. The resultant solution was stirred for 10–15 mins and a solution of pyridinium bromide perbromide (26 g) in acetonitrile (50 ml) was added, maintaining the temperature in the range 0–10°. The resultant suspension was stirred at 0–5° for ca 20 mins. 8% w/v Aqueous sodium bicarbonate solution (70 ml) was added, cautiously, the mixture stirred for 5–10 mins and the layers separated. The aqueous phase was back extracted with dichloromethane (40 ml). The combined organic phases are washed with further 8% w/v sodium bicarbonate solution (70 ml), 2 MHCL (2×70 ml) and water (70 ml), back extracting each wash with dichloromethane (20 ml). The solution was concentrated to 100 ml$^2$ via distillation and ethyl acetate (100 ml) was added. This process was repeated twice. The solution was reconcentrated to 65 ml and allowed to cool to 75°. A solution of tributyl phosphine in ethyl acetate (51 ml, ca 33% wrt TBP) was added over ca 60 mins and the solution heated to reflux. The solution was maintained at reflux for 2 hours. The reaction was allowed to cool to 50° and then seeded with authentic material. The resultant suspension was cooled to 0–5° and aged for 60 min. The product was isolated by vacuum filtration and washed with ethyl acetate:t-butylmethyl ether (1:1, 80 ml), to give the title compound solid which was dried in a vacuum oven at 45° to constant weight.

EXAMPLE 3

(E)-4,6-dichloro-3-(2-oxo-1-phenylpyrrolidin-3-ylidenemethyl)-1H-indole-2-carboxylic acid sodium salt Intermediate 1 (1 g) was added slowly, without stirring, to a two phase system composed of isopropanol (7 ml) and NaOH 32% w/v (1.3 ml). The reaction mixture was heated to reflux and stirred at reflux for 2.5 hr. Water (21 ml) was added dropwise over 30 minutes. The reaction mixture was stirred for 30 minutes at 60° C. then cooled slowly to 10° C.

over 2 hr and further stirred at 10–15° C. for 1 hr. The suspension was then isolated by vacuum filtration and washed with a mixture of isopropanol/water ⅓ (2 ml) and water (12 ml). The solid was dried in a vacuum oven at 40° C. to give the title compound as an off white solid (0.79 g).

What is claimed is:

1. A process for the preparation of the phosphonium compound of formula (I), wherein each of $R_1$, $R_2$ and $R_3$ independently represent a $C_{1-12}$ alkyl or phenyl alkyl group,

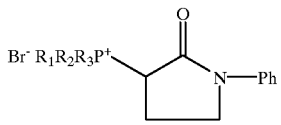

(I)

which comprises reacting N-phenylpyrrolidinone (II), (II)

(III)

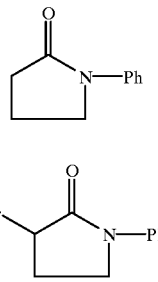

with pyridinium bromide perbromide, in the presence of a tertiary organic base and a suitable lewis acid and then treating the resultant bromo derivative (III),) with the phosphine (IV, $R_1R_2R_3P$) wherein $R_1$, $R_2$ and $R_3$ have the meanings defined above.

2. A process as claimed in claim 1 wherein the lewis acid is trimethylsilyltriflate.

3. A process as claimed in claim 1 wherein the tertiary organic base is N,N,N$^1$N$^1$-tetramethylethylenediamine.

4. A process as claimed in claim 1 wherein the phosphine (IV) is a compound wherein $R_1$, $R_2$ and $R_3$ each independently represent a $C_{1-12}$ alkyl.

5. A process as claimed in claim 1 wherein the phosphine (IV) is tri-n-butylphosphine.

6. A compound of formula (I) as claimed in claim 1 wherein $R_1$, $R_2$ and $R_3$ each independently represent $C_{1-12}$ alkyl.

7. A compound of formula (I) as claimed in claim 1 wherein $R_1$, $R_2$ and $R_3$ each represent an n-butyl group.

8. A process as claimed in claim 2 wherein the tertiary organic base is N,N,N$^1$N$^1$-tetramethylethylenediamine.

9. A process as claimed in claim 2 wherein the phosphine (IV) is a compound wherein $R_1$, $R_2$ and $R_3$ each independently represent a $C_{1-12}$ alkyl.

10. A process as claimed in claim 3 wherein the phosphine (IV) is a compound wherein $R_1$, $R_2$ and $R_3$ each independently represent a $C_{1-12}$ alkyl.

11. A process as claimed in claim 4 wherein the phosphine (IV) is a compound wherein $R_1$, $R_2$ and $R_3$ each independently represent a $C_{1-12}$ alkyl.

12. A process as claimed in claim 2 wherein the phosphine (IV) is tri-n-butylphosphine.

13. A process as claimed in claim 3 wherein the phosphine (IV) is tri-n-butylphosphine.

14. A process as claimed in claim 4 wherein the phosphine (IV) is tri-n-butylphosphine.

* * * * *